United States Patent
Watson

(10) Patent No.: US 9,516,825 B2
(45) Date of Patent: Dec. 13, 2016

(54) ONION VARIETY NUN 08003 ON

(71) Applicant: Nunhems B.V., Nunhem (NL)

(72) Inventor: Rick Watson, Silverton, OR (US)

(73) Assignee: Nunhems B.V., AB Nunhem (NL)

( * ) Notice: Subject to any disclaimer, the term of this patent is extended or adjusted under 35 U.S.C. 154(b) by 0 days.

(21) Appl. No.: 14/953,512

(22) Filed: Nov. 30, 2015

(65) Prior Publication Data

US 2016/0073604 A1 Mar. 17, 2016

(51) Int. Cl.
*A01H 5/04* (2006.01)

(52) U.S. Cl.
CPC ..................................... *A01H 5/04* (2013.01)

(58) Field of Classification Search
None
See application file for complete search history.

(56) References Cited

U.S. PATENT DOCUMENTS

| | | |
|---|---|---|
| 2009/0193545 A1 | 7/2009 | Watson |
| 2011/0041217 A1 | 2/2011 | Watson |

FOREIGN PATENT DOCUMENTS

| | | | |
|---|---|---|---|
| WO | 2013182646 A1 | 12/2013 | |
| WO | 2014076249 A1 | 5/2014 | |

OTHER PUBLICATIONS

Gent et al. (Plant Disease, Jun. 2005, pp. 631-639).*

Acquaah, Principles of Plant Genetics and Breeding, 2007, Blackwell Publishing, ISBN-13: 978-1-4051-3646-4.

US Department of Agriculture, Agricultural Marketing Service, Objective Description of Variety Onion (*Allium cepa*L.) http://www.ams.usda.gov/AMSv1.0/getfile?dDocName=STELDEV3003776.

Upov, Guidelines for the Conduct of Tests for Distinctness, Uniformity and Stability, TG/46/7 (Geneva 2008), http://www.upov.int/edocs/tgdocs/en/tg046.pdf.

Dunstan and Short, "Improved Growth of Tissue Cultures of the Onion, *Allium cepa*", Physiol. Plant, 1977, vol. 41, pp. 70-72.

Santos, Carlos Antonio F, et al., "Similaridade genética entre cultivares de cebola de diferentes tipos e origens, baseada em mercadores AFLP", Hortic. Bras. 2011, vol. 29:1, pp. 32-37.

McCallum, John, et al., "Genetic mapping of a major gene affecting onion bulb fructan content", Theor Appl Genet, 2006, vol. 112, pp. 958-967.

Wijnker et al., "Hybrid recreation by reverse breeding in Arabidopsis thaliana", Nature Protocols, 2014, vol. 9:4, pp. 761-772.

Choi, Pil S., et al., "Genetic transformation and plant regeneration of watermelon using Agrobacterium tumefaciens", Plant Cell Reports, 1994, vol. 13, pp. 344-348.

Pike and Yoo, "A tissue culture technique for the clonal propagation of onion using immature flower buds", Scientia Horticulturae, 1990, vol. 45:1-2, pp. 31-36.

Ellul, P., et al., "The expression of the *Saccharomyces cerevisiae* HAL1 gene increases salt tolerance in transgenic watermelon [Citrullus lanatus (Thunb.) Matsun. & Nakai.]", Theor Appl Genet, 2003, vol. 107, pp. 462-469.

Vos, Pieter, et al., "AFLP: a new technique for DNA fingerprinting", Nucleic Acids Research, 1995, vol. 23:21, pp. 4407-4414.

\* cited by examiner

*Primary Examiner* — Brent Page
*Assistant Examiner* — Jared Shapiro

(57) ABSTRACT

The invention relates to the field of *Allium* in particular to a new variety of onion. designated NUN 08003 ON as well as plants, seeds and bulbs thereof.

17 Claims, No Drawings

ONION VARIETY NUN 08003 ON

FIELD OF THE INVENTION

The present invention relates to the field of plant breeding and, more specifically, to the development of onion variety NUN 08003 ON (or NUN 08003 or NUN 8003 ON or NUN 8003 F1 or NUN 8003 hybrid or 8003 ON or Rhea). The invention further relates to vegetative reproductions of NUN 08003 ON methods for in vitro tissue culture of NUN 08003 ON explants and also to phenotypic variants of NUN 08003 ON. The invention further relates to methods of producing bulbs or bulblets of NUN 08003 ON.

BACKGROUND OF THE INVENTION

The goal of vegetable breeding is to combine various desirable traits in a single variety/hybrid. Such desirable traits may include greater yield, resistance to insects or pests, tolerance to heat and drought, desired earliness, better agronomic quality, higher nutritional value, growth rate and bulb properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

Onions belong to the lily family, Amaryllidaceae, and the genus *Allium*. Alliums comprise a group of perennial herbs having bulbous, onion-scented underground leaves, commonly known as onion bulbs, including such commonly cultivated crops as garlic, chives, and shallots. It also includes ornamental species grown for their flowers.

Onions are an important vegetable world-wide, ranking second among all vegetables in economic importance with an estimated production of over 80 million tons in 2012 (FAOSTAT). The onion is also one of the oldest cultivated vegetables in history. In general, the bulb is harvested and eaten. The common garden onions belong to the species *Allium cepa*. Onions are classified in numerous ways, by basic use, flavor, color, shape of the bulb, and day length. Onions come in white, yellow, and red colors. The bulb may be rounded, flattened, or tapering cylindrical.

Commercial onions include "storage onions", "fresh onions", "pearl or mini onions", and "green onions". "Fresh onions" tend to have a lighter color with a thin skin, a milder, sweeter flavor, and must be eaten fresh as they do not store well. These onions are available in red, yellow, and white colors.

Storage onions are available from harvest, which is at the beginning of August, and are stored and available throughout the winter months up to about March. Storage onions have a darker skin that is thicker than that of a fresh onion. They are also known for intense, pungent flavor, higher percentage of solids and desirable cooking characteristics. These onions are also available in red, yellow and white colors. Not all long day length type (long day type) onions are suitable for storage. A true storage onion is one that can be harvested in late summer or fall, and stored, under proper conditions, until the spring, when the fresh onion crop is again available.

"Spanish onion", "Spanish onions", or "Spanish type" are terms applied to various long-day onions, generally yellow, though some white, and generally varieties that are large and globe-shaped. Spanish onion is commonly applied to various long day type onions of the type grown in western states of the United States (California, Idaho, Oregon, Washington, Colorado) with a bulb size averaging 300-700 grams (g) (typically over 3 inches up to 4 inches but also up to 5 inches in diameter for bulbs classified as "colossal").

Onion varieties initiate bulbing when both the temperature and a minimum number of daylight hours reach certain levels. When onions are first planted, they initially develop their vegetative growth, with no sign of bulb formation until the proper day length for that onion variety triggers the signal to the plant to stop producing above ground vegetative growth and start forming a bulb. Onions are thus sensitive to the hours of daylight and darkness they receive, and for most varieties it is only when the specific combination of daylight and darkness is reached, that the bulb starts to form. Onions are therefore classified by the degree of day length that will initiate bulb formation. Onions are described as short-, intermediate-, and long-day length types. Short day means that bulbing will initiate at 11 to 12 hours of daylight. Intermediate day is used for onions bulbing at 12 to about 14 hours of daylight. Long day onions require about 14 or more hours of daylight for bulb formation to start.

Growers producing onions in more northerly climates plant long-day length onions. Daylight length varies greatly with latitude, and at higher latitudes long-day onions will produce sufficient top growth before the day length triggers bulbing to produce a large bulb. A short-day onion grown in the North (higher latitudes) will bulb too early and produce relatively small bulbs.

Short day onions are preferred for southern areas such as southern Texas, southern California and Mexico. If a long day type onion is planted in such a short day climate, it may never experience enough day length to trigger the bulbing process.

Onions are also classified on flavor, with the common designations of sweet, mild, and pungent. The flavor of the onion is a result of both the type of onion and the growing conditions. For instance, soils containing a high amount of sulfur result in more pungent flavored onions. Sweetness in onions is caused by the sugars glucose, fructose and sucrose. Onions also contain polymers of fructose called fructans. Onion cultivars differ quite markedly in the relative amounts of sucrose, glucose, fructose and fructans which they contain. They also differ in sugars according to length of storage and location in the bulb. Short day cultivars, which are poor storers, tend to have higher levels of sucrose, fructose and glucose, but hardly any of the fructans. In contrast, long day type cultivars and intermediate storage cultivars such as Pukekohe Longkeeper have less sucrose, glucose and fructose and higher amounts of fructans.

Short day varieties do not keep well in storage conditions, and the pungency of short day varieties can climb considerably during storage. Present production in North America and Europe allows harvest of short day onions from mild winter regions from November through April. Long day onions are available fresh in the late summer and as storage onions from September through March, or even year round, have not been available in low pungency varieties (with the exception of U.S. patent application Ser. No. 12/861,740 which is based on patent application Ser. No. 12/020,360). Sweet onions must be imported from the southern hemisphere to fill the gap in sweet onion production (November-February). In the United States, regions like Georgia and Texas produce short day onions from March to June, while low pungency onions available from November to February are short day onions, produced in the southern hemisphere.

The use of a type of onion is depending on a customer's preference for taste, aroma, appearance and color of an onion. There is thus a need for new short day onions with new appearance and color properties.

SUMMARY OF THE INVENTION

In one aspect of the invention, a seed of onion variety NUN 08003 ON is provided, wherein a representative sample of said seed has been deposited under Accession Number NCIMB 42621. The onion seed of the invention may be provided as an essentially homogeneous population of onion seed. Therefore, seed of the invention may be defined as forming at least about 97% of the total seed, including at least about 98%, 99% or more of the seed. The population of onion seed may be particularly defined as being essentially free from non-hybrid seed. The seed population may be separately grown to provide an essentially homogeneous population of onion plants according to the invention. Also encompassed are plants grown from seeds of onion variety NUN 08003 ON and plant parts thereof such as a leaf, pollen, an ovule, a bulb and a cell. The invention also provides for a plurality of seeds of the new variety, plants produced from growing the seeds of the new variety NUN 08003 ON, and progeny of any of these.

The invention also concerns plants of onion variety NUN 08003 ON. The invention also provides for a plurality of seeds of the new variety, plants produced from growing the seeds of the new variety NUN 26357 MEM, and progeny of any of these. Another aspect refers to an onion plant, or a part thereof, having all or all but 1, 2, 3, 4, or 5 the physiological and morphological characteristics of an onion plant of onion variety NUN 08003 ON.

In one aspect, such progeny have all the physiological and morphological characteristics of onion variety NUN 08003 ON when grown under the same environmental conditions. In another aspect such progeny have all the physiological and morphological characteristics as listed in Table 1 and/or 2 as onion variety NUN 08003 ON when measured under the same environmental conditions (i.e. evaluated at significance levels of 1%, 5% or 10% significance, which can also be expressed as a p value).

In another aspect a plant of the invention or said progeny plants has/have 1, 2, 3, 4 or more or all of the distinguishing characteristics selected from the group consisting of: 1) bulb height; 2) bulb diameter; 3) Sheath column length (height from soil line to base of lowest succulent leaf); 4) Plant height above soil line to highest point of any foliage; 5) adaptation range; 6) sheath diameter (at mid-length); 7) bulb weight; 8) maturity; and 9) leaf thickness. In another aspect a plant of the invention has in addition to the 1, 2, 3, 4 or more or all of the above-cited distinguishing characteristics, 3, 4, 5, 6, 7, or more, or all of the other (average) characteristics as listed in Table 1 and/or 2.

Further, an onion bulb produced on a plant grown from these seeds is provided.

In yet another embodiment of the invention, a plant having one, two or three physiological and/or morphological characteristics which are different from those of NUN 08003 ON and which otherwise has all the physiological and morphological characteristics of NUN 08003 ON as listed in Table 1 and/or 2, wherein a representative sample of seed of variety NUN 08003 ON has been deposited under Accession Number NCIMB 42621, is provided.

Further, a vegetatively propagated plant of variety NUN 08003 ON, or a part thereof, is provided having all the morphological and physiological characteristics of NUN 08003 ON when grown under the same environmental conditions.

Also a plant part derived from variety NUN 08003 ON is provided, wherein said plant part is selected from the group consisting of: bulbs, harvested bulbs, parts of bulbs, scales, parts of scales, bulblets, parts of bulblets, leaves, parts of leaves, pollen, ovule, cells, petioles, fruits, shoots or parts thereof, stems or parts thereof, roots or parts thereof, cuttings, seeds, parts of seeds, seedcoat, hypocotyl, cotyledon, flowers or parts thereof, and flower. Bulbs are particularly important plant parts.

In another aspect of the invention, a tissue culture of regenerable cells of a plant of variety NUN 08003 ON is provided. The tissue culture will preferably be capable of regenerating plants capable of expressing all of the physiological and morphological characteristics of a plant of the invention, and of regenerating plants having substantially the same genotype as other such plants. Examples of some such physiological and morphological characteristics include those traits set forth in Table 1 and/or 2 herein. The regenerable cells in such tissue cultures may be derived, for example, from embryos, meristems, cotyledons, pollen, leaves, anthers, roots, root tips, pistil, flower, seed and stalk. Thus, a tissue culture may comprise regenerable cells from embryos, meristems, cotyledons, pollen, leaves, anthers, roots, root tips, pistil, flower, seed and bulbs. Still further, the present invention provides onion plants regenerated from a tissue culture of the invention, the plants having all the physiological and morphological characteristics of a plant of the invention.

The invention also concerns methods for vegetative propagating of a plant of the invention. In certain embodiments, the method comprises the steps of: (a) collecting tissue capable of being propagated from a plant of the invention; (b) cultivating said tissue to obtain proliferated shoots; and (c) rooting said proliferated shoots to obtain rooted plantlets. In some of these embodiments, the method further comprises growing plants from said rooted plantlets.

In yet another aspect of the invention, processes are provided for producing onion seeds, plants and bulbs, which processes generally comprise crossing a first parent onion plant with a second parent onion plant, wherein at least one of the first or second parent onion plants is a plant of the variety designated NUN 08003 ON.

These processes may be further exemplified as processes for preparing hybrid onion seed or plants, wherein a first onion plant is crossed with a second onion plant of a different, distinct variety to provide a hybrid that has, as one of its parents, the onion plant variety NUN 08003 ON.

In another embodiment of the invention, onion variety NUN 08003 ON is crossed to produce onion seed derived of the variety designated NUN 08003 ON. In any cross herein, either parent may be the male or female parent. In these processes, crossing will result in the production of seed. The seed production occurs regardless of whether the seed is collected or not.

In one embodiment of the invention, the first step in "crossing" comprises planting seeds of a first and a second parent onion plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of the first and the second parent onion plants into plants that bear flowers. A third step may comprise preventing self-pollination of the plants, such as by emasculating the male portions of flowers, (e.g., treating or manipulating the flowers to produce an emasculated parent onion plant). Self-incompatibility systems may also be used in some hybrid crops for the same purpose. Self-incompatible plants still shed viable pollen and can pollinate plants of other varieties but are incapable of pollinating themselves or other plants of the same variety.

A fourth step for a hybrid cross may comprise crosspollination between the first and second parent onion plants. In certain embodiments, pollen may be transferred manually or by the use of insect vectors. Yet another step comprises harvesting the seeds from at least one of the parent onion plants. The harvested seed can be grown to produce an onion plant or hybrid onion plant.

The present invention also provides the onion seeds and plants produced by a process that comprises crossing a first parent onion plant with a second parent onion plant, wherein at least one of the first or second parent onion plants is a plant provided herein, such as from variety NUN 08003 ON. In another embodiment of the invention, onion seed and plants produced by the process are first filial generation (F1) onion seed and plants produced by crossing a plant in accordance with the invention with another, distinct plant.

The present invention further contemplates plant parts of such an F1 onion plant, and methods of use thereof. Therefore, certain exemplary embodiments of the invention provide an F1 onion plant and seed thereof.

WO2013182646 which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed, comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of NUN 08003 ON (i.e. is progeny of NUN 0126 ON) because the seed coat is genetically identical to NUN 08003 ON. In one embodiment, the present invention relates to a seed coat comprising maternal tissue of NUN 08003 ON. In another embodiment the invention relates to an onion seed comprising a seed coat that comprises maternal tissue from NUN 08003 ON.

In still yet another aspect, the present invention provides a method of producing a plant or a seed derived from variety NUN 08003 ON, the method comprising the steps of: (a) preparing a progeny plant derived from said variety by crossing a plant of variety NUN 08003 ON with a second plant; and (b) selfing the progeny plant or crossing it to the second plant or to a third plant to produce a seed of a progeny plant of a subsequent generation.

The method may additionally comprise: (c) growing a progeny plant of a further subsequent generation from said seed of a progeny plant of a subsequent generation and selfing the progeny plant of a subsequent generation or crossing it to the second, the third, or a further plant; and repeating the steps for 3 or more times, e.g., an additional 3-10 generations to produce a further plant derived from the aforementioned starting variety. The further plant derived from variety NUN 08003 ON may be an inbred variety, and the aforementioned repeated crossing steps may be defined as comprising sufficient inbreeding to produce the inbred variety. In the method, it may be desirable to select particular plants resulting from step (c) for continued crossing according to steps (b) and (c). By selecting plants having one or more desirable traits, a plant is obtained which possesses some of the desirable traits of the starting plant as well as potentially other selected traits.

One aspect of the invention refers to a method of producing an onion plant comprising crossing an onion plant of variety NUN 08003 ON with a second onion plant one or more times. This method comprises in one embodiment selecting progeny from said crossing.

For example, in certain embodiments, the invention provides methods of introducing a desired trait into a plant of the invention comprising: (a) crossing a plant of variety NUN 08003 ON with a second onion plant that comprises a desired trait to produce F1 progeny, (b) selecting an F1 progeny that comprises the desired trait(s), e.g., one, two, three or more desired trait(s), (c) crossing the selected F1 progeny with a plant of variety NUN 08003 ON to produce backcross progeny, and (d) selecting backcross progeny comprising the desired trait(s) and which otherwise has all the physiological and morphological characteristics of variety NUN 08003 ON. Optionally, steps (c) and (d) can be repeated one or more times, e.g., three or more times such as three, four, five, six or seven times, in succession to produce selected fourth, fifth, sixth, seventh or eighth or higher backcross progeny that comprises the desired trait. The invention also provides onion plants produced by these methods.

In still yet another aspect, the invention provides a method of determining the genotype of a plant of the invention comprising detecting in the genome of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

In one embodiment of the invention, the invention provides a method for producing a seed of a variety derived from NUN 08003 ON comprising the steps of (a) crossing an onion plant of variety NUN 08003 ON with a second onion plant; and (b) allowing seed of an onion plant derived from variety NUN 08003 ON to form. This method can further comprise steps of (c) crossing a plant grown from said variety NUN 08003 ON-derived onion seed with itself or a second onion plant to yield additional variety NUN 08003 ON-derived onion seed; (d) growing said additional variety NUN 08003 ON-derived onion seed of step (c) to yield additional variety NUN 08003 ON-derived onion plants; and optionally (e) repeating the crossing and growing steps of (c) and (d) to generate further variety NUN 08003 ON-derived onion plants. For example, the second onion plant is of an inbred onion variety.

In certain embodiments, the present invention provides a method of producing onions comprising: (a) obtaining a plant of the invention, wherein the plant has been cultivated to maturity, and (b) collecting an onion bulb from said plant.

Any embodiment discussed herein with respect to one aspect of the invention applies to other aspects of the invention as well, unless specifically noted.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DEFINITIONS

In the description and tables herein, a number of terms are used. In order to provide a clear and consistent understanding of the specification and claims, the following definitions are provided:

The term "about" in relation to a particular value refers to said value +/−5%, i.e. to a range between said value minus 5% of said value and said value plus 5% of said value.

"Onion plant" or "onion" is a plant of genus *Allium* or a part thereof (e.g. a bulb). Onion includes, e.g., *Allium aggregatum* (e.g., chalottes and potato onion), *Allium cepa* and *Allium fistulosum*, as well as crossbreds thereof, and hybrids such as *Allium×proliferum, Allium×wakegi*, and the triploid onion *Allium×cornutum*.

"Biennial plant" means that *Allium cepa* L. produces a bulb in the first season and seeds in the second.

"Cultivated onion" refers to plants of *Allium*, i.e. varieties, breeding lines or cultivars of the species *Allium cepa* as well as crossbreds with *Allium aggregatum* and *Allium fistulosum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of *Allium* and related species.

The terms "Onion plant designated NUN 08003 ON", "NUN 08003" "08003 ON" or "variety designated NUN 08003 ON" are used interchangeably herein and refer to an onion plant of variety NUN 08003 ON, representative seed of which having been deposited under Accession Number NCIMB 42621.

"Tissue culture" refers to a composition comprising isolated cells of the same or a different type or a collection of such cells organized into parts of a plant. Tissue culture of various tissues of onion and regeneration of plants therefrom is well known and widely published (see, e.g., Dunstan and Short (1977) Physiol, Plant, 41: 70-72.; Pike and Yoo, Scientia Horticulturae, 45 (1990) 31-36. Similarly, the skilled person is well-aware how to prepare a "cell culture".

"USDA descriptors" are the plant variety descriptors for onion as published by U.S. Department of Agriculture, Agricultural Marketing Service, Science and Technology, Plant Variety Protection Office, Beltsville, Md. 20705 (available on the world wide web at ams.usda.gov) in the "Objective description of Variety Onion *Allium cepa* L.", ST-470-16 and which can be downloaded from the world wide web at ams.usda.gov/AMSv1.0/getfile?dDocName=STELDEV3003776.

"UPOV descriptors" are the plant variety descriptors for onion described in the "Guidelines for the Conduct of Tests for Distinctness, Uniformity and Stability, TG/46/7 (Geneva 2009), as published by UPOV (International Union for the Protection of New Varieties and Plants, available on the world wide web at upov.int) and which can be downloaded from the world wide web at upov.int under edocs/tgdocs/en/tg046.pdf and is herein incorporated by reference in its entirety.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS color chart: 2007 (The Royal Horticultural Society, PO Box 313 London SW1P2PE).

"Genotype" refers to the genetic composition of a cell or organism.

"Phenotype" refers to the detectable characteristics of a cell or organism, which characteristics are the manifestation of gene expression.

As used herein, the term "plant" includes the whole plant or any parts or derivatives thereof, preferably having the same genetic makeup as the plant from which it is obtained, such as plant organs (e.g. harvested or non-harvested onion bulbs (tubers), leaves etc.), plant cells, plant protoplasts, plant cell and/or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, flowers, leaves, seeds, clonally propagated plants, roots, stems, root tips, grafts, parts of any of these and the like. Also any developmental stage is included, such as seedlings, cuttings prior or after rooting, mature plants or leaves.

By "bulb" or "onion bulb" is meant the (commercially) (harvested or harvestable) edible portion of the onion plant. An onion bulb comprises an apex and concentric, enlarged fleshy leaf bases, also called fleshy scale leaves (see, e.g., FIG. 1). Onion bulbs may be developing onion bulbs or mature onion bulbs. A small bulb or a bulb early in its development or a secondary bulb developing on the main bulb may be described as a bulblet.

"Harvested plant material" refers herein to plant parts which have been collected for further storage and/or further use.

"Harvested seeds" refers to seeds harvested from a line or variety, e.g. produced after self-fertilization or cross-fertilization and collected.

"REFERENCE VARIETY" refers to the variety Cometa from company Nunhems (currently Bayer Crop Science—Vegetable seeds) which has been planted in a trial together with NUN 08003 ON. USDA descriptors of NUN 08003 ON were compared to the USDA descriptors of REFERENCE VARIETY.

"Flavor" refers to the sensory impression of a food or other substance, especially onion bulb or bulb part and is determined mainly by the chemical senses of taste and smell. Flavor is influenced by texture properties and by volatile and/or non-volatile chemical components (organic acids, lipids, carbohydrates, etc.). Pungency and sweetness are non-limiting examples of flavor components of an onion bulb.

"Planting" or "planted" refers to seeding (direct sowing) or transplanting seedlings (plantlets) into a field by machine or hand.

A plant having "all the physiological and morphological characteristics" of a referred-to-plant means a plant having the physiological and morphological characteristics of the referred-to-plant when grown under the same environmental conditions; the referred-to-plant can be a plant from which it was derived, e.g. the progenitor plant, the parent, the recurrent parent, the plant used for tissue- or cell culture, etc.

A plant having "essentially all the physiological and morphological characteristics" of a referred-to-plant means a plant having at least 5 (e.g. 6, 7, 8, 9 or all) of the distinguishing physiological and morphological characteristics (distinguishing characteristics as herein defined) when grown under the same environmental conditions of the referred-to-plant (e.g. a plant from which it was derived such as the progenitor plant, the parent, the recurrent parent, the plant used for tissue- or cell culture, etc.). Alternatively, a plant having "essentially all the physiological and morphological characteristics" of a referred-to-plant means a plant having all the characteristics as listed in Table 1 and/or 2 when grown under the same environmental conditions as a referred-to-plant (e.g. a plant from which it was derived such as the progenitor plant, the parent, the recurrent parent, the plant used for tissue- or cell culture, etc.). In another embodiment, a plant having "essentially all the physiological and morphological characteristics" of a referred-to-plant means a plant having all but 1, 2, 3, 4 or 5 of the characteristics as listed in Table 1 and/or 2 when grown under the same environmental conditions as a referred-to-plant (e.g. a plant from which it was derived such as the progenitor plant, the parent, the recurrent parent, the plant used for tissue- or cell culture, etc.).

For NUN 08003 ON the distinguishing characteristics are 1) bulb height; 2) bulb diameter; 3) Sheath column length (height from soil line to base of lowest succulent leaf); 4) Plant height above soil line to highest point of any foliage; 5) adaptation range; 6) sheath diameter (at mid-length); 7) bulb weight; 8) maturity; and 9) leaf thickness.

In certain embodiments the plant of the invention has all the physiological and morphological characteristics, except for certain characteristics mentioned, e.g. the characteristic(s) derived from a converted or introduced gene or trait and/or except for the characteristics which differ.

Similarity between different plants is defined as the number of distinguishing characteristics (or the characteristics as listed in Table 1 and/or 2) that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions.

A plant having one or more "essential physiological and/or morphological characteristics" or one or more "distinguishing characteristics" refers to a plant having (or retaining) one or more of the characteristics mentioned in Table 1 and/or 2 when grown under the same environmental conditions that distinguish NUN 08003 ON from the most similar varieties (such as reference variety Cometa), such as but not limited to average bulb size, bulb flavor, color and texture, maturity, umbel diameter or average leaf length.

"Distinguishing characteristics" or "distinguishing morphological and/or physiological characteristics" refers herein to the characteristics which are distinguishing between NUN 08003 ON and other onion varieties, such as reference variety Cometa, when grown under the same environmental conditions, especially the following characteristics: 1) bulb height; 2) bulb diameter; 3) Sheath column length (height from soil line to base of lowest succulent leaf); 4) Plant height above soil line to highest point of any foliage; 5) adaptation range; 6) sheath diameter (at mid-length); 7) bulb weight; 8) maturity; and 9) leaf thickness In one aspect, the distinguishing characteristics further include at least one, two, three or more (or all) of the characteristics listed in Table 1.

Thus, an onion plant "comprising the distinguishing characteristics of NUN 08003 ON" refers herein to an onion plant which does not differ significantly from NUN 08003 ON in characteristics 1) to 5) above. In a further aspect the onion plant further does not differ significantly from NUN 08003 ON in one or more, or all characteristics 6) to 9) as mentioned above. In yet a further aspect the onion plant further does not differ in at least one, two, three, four, five or six characteristics selected from the characteristics listed in Table 1 and/or 2. In still another aspect the onion plant does not differ in any of the distinguishing characteristics 1) to 9) listed above.

The physiological and/or morphological characteristics mentioned above are commonly evaluated at significance levels of 1%, 5% or 10% % if they are numerical, or for identical type if not numerical, when measured under the same environmental conditions. For example, a progeny plant of NUN 08003 ON may have one or more (or all) of the essential physiological and/or morphological characteristics of NUN 08003 ON listed in Table 1 and/or 2, as determined at the 5% significance level (i.e. p ~0.05) when grown under the same environmental conditions.

"Maturity" refers to the development stage of an onion bulb when said onion bulb has fully developed (reached its final size). In particular embodiments "maturity" is defined as the mature state of bulb development and optimal time for harvest. Typically, maturity of a bulb is reached when the vegetative phase of an onion plant is over and leaves and neck of the onion plant dry out.

"Harvest maturity" is referred to as the stage at which an onion bulb is ready for harvest or the optimal time to harvest the bulb. In one embodiment, harvest maturity is the stage where 25-50% of the onion leaf tops have fallen over.

"Yield" means the total weight of all onion bulbs harvested per surface unit or per plant of a particular line or variety. It is understood that "yield" expressed as weight of all onion bulbs harvested per hectare can be obtained by multiplying the number of plants per hectare times the "yield per plant".

"Marketable yield" means the total weight of all marketable onion bulb harvested per hectare of a particular line or variety, i.e. bulbs suitable for being sold for fresh consumption, having acceptable shape, moisture, pungency etc., and no or very low levels of deficiencies.

As used herein, a "mature onion bulb" refers to any onion bulb that is ready for harvest. Generally, when 25-50% of the onion leaf tops have fallen over, the onion is ready for harvest.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Plant line" is for example a breeding line which can be used to develop one or more varieties.

"Hybrid variety" or "F1 hybrid" refers to the seeds of the first generation progeny of the cross of two non-isogenic plants. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) a bulb or part thereof, leaf, pollen, embryo, cotyledon, hypocotyl, cells, protoplasts, meristematic cell, root, root tip, pistil, anther, flower, shoot tip, shoot, stem, petiole, seed coat, etc. When a whole plant is regenerated by vegetative propagation, it is also referred to as a vegetative propagation.

The terms "gene converted" or "conversion plant" in this context refer to onion plants which are often developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of an onion variety are recovered in addition to the characteristics of the single locus having been transferred into the variety via the backcrossing technique and/or by genetic transformation.

"Progeny" as used herein refers to plants derived from a plant designated NUN 08003 ON. Progeny may be derived by regeneration of cell culture or tissue culture or parts of a plant designated NUN 08003 ON or selfing of a plant designated NUN 08003 ON or by producing seeds of a plant designated NUN 08003 ON. In further embodiments, progeny may also encompass plants derived from crossing of at least one plant designated NUN 08003 ON with another onion plant of the same or another variety or (breeding) line, or with a wild onion plant, backcrossing, inserting of a locus into a plant or selecting a plant comprising a mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above.

The term "traditional breeding techniques" encompasses herein crossing, selfing, selection, double haploid production, embryo rescue, protoplast fusion, marker assisted selection, mutation breeding, tissue propagation etc. as known to the breeder (i.e. methods other than genetic modification/transformation/transgenic methods), by which, for example, a genetically heritable trait can be transferred from one onion line or variety to another.

"Crossing" refers to the mating of two parent plants.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant". Onion varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

"Selfing" refers to self-pollination of a plant, i.e., the transfer of pollen from the anther to the stigma of the same plant.

"Locus" (plural loci) refers to the specific location of a gene or DNA sequence on a chromosome. A locus may confer a specific trait.

"Marker" refers to a readily detectable phenotype, preferably inherited in codominant fashion (both alleles at a locus in a diploid heterozygote are readily detectable), with no environmental variance component, i.e., a heritability of one (1).

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

"Transgene" or "chimeric gene" refers to a genetic locus comprising a DNA sequence which has been introduced into the genome of an onion plant by transformation. A plant comprising a transgene stably integrated into its genome is referred to as "transgenic plant".

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for onion described herein. The mean, if not indicated otherwise within this application, refers to the arithmetic mean of measurements on at least 10 different, randomly selected plants of a variety or line.

"Substantially equivalent" refers to a characteristic that, when compared, does not show a statistically significant difference (e.g., p=0.05) from the mean.

DETAILED DESCRIPTION OF THE INVENTION

The present invention relates to a *Allium cepa* variety, referred to as NUN 08003 ON, which has higher bulbs height than reference variety Cometa, larger bulb diameter than reference variety Cometa, shorter sheath column than reference variety Cometa, shorter plant height above soil line to highest point of any foliage than reference variety Cometa, a smaller adaptation range than reference variety Cometa, thicker sheath diameter (at mid-length) than reference variety Cometa, higher bulb weight than reference variety Cometa, slower maturity than reference variety Cometa and thinner leaf than reference variety Cometa. Also encompassed by the present invention are progeny of NUN 08003 ON and methods of producing plants in accordance with the present invention.

An onion plant of NUN 08003 ON differs from the most similar reference variety Cometa in one or more characteristics (referred herein to as "distinguishing characteristics" or "distinguishing morphological and/or physiological characteristics" (or essential physiological and/or morphological characteristics) selected from 1) bulb height; 2) bulb diameter; 3) Sheath column length (height from soil line to base of lowest succulent leaf); 4) Plant height above soil line to highest point of any foliage; 5) adaptation range; 6) sheath diameter (at mid-length); 7) bulb weight; 8) maturity; and 9) leaf thickness.

It is understood that "significant" differences refer to statistically significant differences, when comparing the characteristic between two plant lines or varieties when grown under the same conditions. Preferably at least about 10, 15, 20 or more plants per line or variety are grown under the same conditions (i.e. side by side) and characteristics are measured on at least about 10, 15, 20 or more randomly selected plant or plant parts to obtain averages. Thus, physiological and morphological characteristics or traits are commonly evaluated at a significance level of 1%, 5% or 10%, when measured in plants grown under the same environmental conditions.

Thus, in one aspect, the invention provides seeds of the onion variety designated NUN 08003 ON wherein a representative sample of seeds of said variety was deposited under the Budapest Treaty, with Accession number NCIMB 42621. Seeds of NUN 08003 ON are obtainable by crossing the male parent with the female parent and harvesting the seeds produced on the female parent. The resultant NUN 08003 ON seeds can be grown to produce NUN 08003 ON plants. In one embodiment a plurality of NUN 08003 ON seeds are packaged into small and/or large containers (e.g., bags, cartons, cans, etc.). The seeds may be disinfected, primed and/or treated with various compounds, such as seed coatings or crop protection compounds.

Also provided are plants of onion variety NUN 08003 ON, or a bulb or other plant part thereof, produced from seeds, wherein a representative sample of said seeds has been deposited under the Budapest Treaty, with Accession Number NCIMB 42621. Also included is a cell culture or tissue culture produced from such a plant It is understood that such tissue or cell culture comprising cells or protoplasts from the plant of the invention can be obtained from a plant part selected from the group consisting of embryos, meristems, cotyledons, hypocotyl, pollen, leaves, anthers, roots, root tips, bulbs, scales, pistil, petiole, flower, fruit, seed, stem and stalks. In one embodiment a plant regenerated from such a cell or tissue culture said plant expressing all the morphological and physiological characteristics of NUN 08003 ON.

In one embodiment the invention provides a onion plant regenerated from the tissue or cell culture of NUN 08003 ON, wherein the plant has all of the physiological and morphological characteristics of NUN 08003 ON as listed in Table 1 and/or 2 when determined at the 5% significance level. In another embodiment, the invention provides a onion plant regenerated from the tissue or cell culture of NUN 08003 ON, wherein the plant has all of the physiological and morphological characteristics of NUN 08003 ON when determined at the 5% significance level.

Plants of NUN 08003 ON can be produced by seeding directly in the ground (e.g., field) or by germinating the seeds in controlled environment conditions (e.g., greenhouses) and then transplanting the seedlings into the field. For example, the seed can be sown into prepared seed beds where they will remain for the entire production of the crop. Alternatively, the onion seed may be planted or transplanted in prepared mounds.

In another aspect, the invention provides for a onion plant of variety NUN 08003 ON, a representative sample of seed from said variety has been deposited under the Budapest Treaty, with Accession number NCIMB 42621.

In other aspects, the invention provides for a bulb or parts thereof of onion variety NUN 08003 ON, or a plant part, such as pollen, flowers, shoots or cuttings of variety NUN 08003 ON or parts thereof.

In one embodiment any plant of the invention comprises at least 3, 4, 5 or more, e.g. 6, 7, 8, 9 or all of the following morphological and/or physiological characteristics (i.e. distinguishing characteristics (average values; measured at harvest or market maturity, as indicated on the USDA Objective description of variety—Onion (unless indicated otherwise), when grown under the same environmental conditions): 1) bulb height; 2) bulb diameter; 3) Sheath column length (height from soil line to base of lowest succulent leaf); 4) Plant height above soil line to highest point of any foliage; 5) adaptation range; 6) sheath diameter (at mid-length); 7) bulb weight; 8) maturity; and 9) leaf thickness.

In still another aspect the invention provides a method of producing a onion plant, comprising crossing a plant of onion variety NUN 08003 ON with a second onion plant one or more times, and selecting progeny from said crossing.

In yet another aspect the invention provides a method of producing a onion plant, comprising selfing a plant of onion variety NUN 08003 ON one or more times, and selecting progeny from said selfing.

In other aspects, the invention provides for progeny of variety NUN 08003 ON such as progeny obtained by further breeding NUN 08003 ON. Further breeding NUN 08003 ON includes selfing NUN 08003 ON one or more times and/or cross-pollinating NUN 08003 ON with another onion plant or variety one or more times. In particular, the invention provides for progeny that retain all the essential morphological and physiological characteristics of NUN 08003 ON or that retain one or more (e.g. 1) to 5) or 1) to 9) or all) of the distinguishing characteristics of the onion type described further above, or, in another embodiment, progeny that retain all morphological and physiological characteristics of NUN 08003 ON as listed in Table 1 and/or 2; when grown under the same environmental conditions, when determined at the 5% significance level. In another aspect, the invention provides for vegetative reproductions of the variety and plants having all but 1, 2, or 3 of the physiological and morphological characteristics of NUN 08003 ON (e.g. as listed in Table 1 and/or 2).

The morphological and/or physiological differences between plants according to the invention, i.e. NUN 08003 ON or progeny thereof, or plants having all but 1, 2, or 3 of the physiological and morphological characteristics of NUN 08003 ON (as listed in Table 1 and/or 2); and other known varieties can easily be established by growing NUN 08003 ON next to the other varieties (in the same field, under the same environmental conditions), preferably in several locations which are suitable for said onion cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby maturity, leaf shape, leaf color, flower size and color, bulb type, bulb color, bulb size, bulb shape, onion sweetness and pungency, disease resistance, insect resistance, can be measured and directly compared for species of *Allium cepa*.

The morphological and physiological characteristics (and distinguishing characteristics) of NUN 08003 ON, are provided in Table 1 and/or 2. Encompassed herein are also plants derivable from NUN 08003 ON (e.g. by selfings and/or crossing and/or backcrossing with NUN 08003 ON and/or progeny thereof) comprising all the physiological and morphological characteristics of NUN 08003 ON listed in Table 1 and/or 2 as determined at the 5% significance level when grown under the same environmental conditions and/or comprising one or more (or all; or all except one, two or three) of the distinguishing characteristics as determined at the 5% significance level when grown under the same environmental conditions.

Also at-harvest and/or post-harvest characteristics of bulbs can be compared, such as storage holding quality or scale retention, can be measured using known methods.

The morphological and/or physiological characteristics may vary somewhat with variation in the environment (such as temperature, light intensity, day length, humidity, soil, fertilizer use), which is why a comparison under the same environmental conditions is preferred. Colors can best be measured against The Munsell Book of Color (Munsell Color Macbeth Division of Kollmorgan Instruments Corporation) or using the Royal Horticultural Society Chart (World wide web at rhs.org.uk/Plants/RHS-Publications/RHS-colour-charts).

In a preferred embodiment, the invention provides for onion bulbs of variety NUN 08003 ON, or a part of the bulb. In another embodiment, the invention provides for a container comprising or consisting of a plurality of harvested onion bulbs of NUN 08003 ON, or progeny thereof. In yet a further embodiment, the invention provides for a method of producing a new onion plant. The method comprises crossing a plant of the invention NUN 08003 ON, or a plant comprising all but 1, 2, or 3 of the morphological and physiological characteristics of NUN 08003 ON (as listed in Table 1 and/or 2), or a progeny plant thereof, either as male or as female parent, with a second onion plant (or a wild relative of onion) one or more times, and/or selfing a onion plant according to the invention i.e. NUN 08003 ON, or a progeny plant thereof, one or more times, and selecting progeny from said crossing and/or selfing. The second onion plant may for example be a line or variety of the species *Allium cepa*, or other *Allium* species.

Progeny are a later generation (of seeds) produced from the first cross of the F1 hybrid with another plant (F2) or with itself (S2), or any further generation produced by crossing and/or selfing (F3, F4 , etc.) and/or backcrossing (BC2, BC3, etc.) one or more selected plants of the F2 and/or S2 and/or BC2 generation (or plants of any further generation, e.g. the F3) with another onion plant (and/or with a wild relative of onion). Progeny may have all the physiological and morphological characteristics of onion variety NUN 08003 ON when grown under the same environmental conditions and/or progeny may have (be selected for having) one or more of the distinguishing characteristics of onion of the invention. Using common breeding methods such as backcrossing or recurrent selection, one or more specific characteristics may be introduced into NUN 08003 ON, to provide or a plant comprising all but 1, 2, or 3 or more of the morphological and physiological characteristics of NUN 08003 ON (as listed in Table 1 and/or 2).

The invention provides for methods of producing plants which retain all the morphological and physiological characteristics of NUN 08003 ON. The invention provides also for methods of producing a plant comprising all but 1, 2, or 3 or more of the morphological and physiological characteristics of NUN 08003 ON (e.g. as listed in Table 1 and/or 2), but which are still genetically closely related to NUN 08003 ON. The relatedness can, for example be determined by fingerprinting techniques (e.g., making use of isozyme markers and/or molecular markers such as SNP markers, AFLP markers, microsatellites, minisatellites, RAPD markers, RFLP markers and others). A plant is "closely related" to NUN 08003 ON if its DNA fingerprint is at least 80%, 90%, 95% or 98% identical to the fingerprint of NUN 08003 ON. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (SANTOS, CAF et al. *Hortic. Bras.* [online] 2011, vol. 29, n. 1, pp. 32-37.). The invention also provides plants and varieties obtained by these methods. Plants may be produced by crossing and/or selfing, or alternatively, a plant may simply be identified and selected amongst NUN 08003 ON plants, or progeny thereof, e.g. by identifying a variant within NUN 08003 ON or progeny thereof (e.g. produced by selfing) which variant differs from NUN 08003 ON in one, two or three of the morphological and/or physiological characteristics (e.g. in one, two or three distinguishing characteristics), e.g. those listed in Table 1 and/or 2 or others. In one embodiment the invention provides a onion plant having a Jaccard's Similarity index with NUN 08003 ON of at least 0.8, e.g. at least 0.85, 0.9, 0.95, 0.98 or even at least 0.99.

By crossing and/or selfing also (one or more) single traits may be introduced into the variety of the invention i.e. NUN 08003 ON (e.g., using backcrossing breeding schemes), while retaining the remaining morphological and physiological characteristics of NUN 08003 ON and/or while retaining one or more distinguishing characteristics. A single trait converted plant may thereby be produced. For example, disease resistance genes may be introduced, genes responsible for one or more quality traits, yield, etc. Both single genes (dominant or recessive) and one or more QTLs (quantitative trait loci) may be transferred into NUN 08003 ON by breeding with NUN 08003 ON.

Any pest or disease resistance genes may be introduced into a plant according to the invention, i.e. NUN 08003 ON, progeny thereof or into a plant comprising all but 1, 2, or 3 or more of the morphological and physiological characteristics of NUN 08003 ON (e.g. as listed in Table 1 and/or 2). Resistance to one or more of the following diseases is preferably introduced into plants of the invention: Black Mold, Neck Mold, Puple Blotch, Smut, Mildew, Pink root, Smudge, Yellow dwarf and *Thrips*. Other resistance genes, against pathogenic viruses, fungi, bacteria, nematodes, insects or other pests may also be introduced.

Thus, invention also provides a method for developing a onion plant in a onion breeding program, using a onion plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 08003 ON or progeny thereof, or a plant comprising all but 1, 2, or 3 or more of the morphological and physiological characteristics of NUN 08003 ON (e.g. as listed in Table 1 and/or 2), with a different onion plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. McCallum et al., Theor Appl Genet (2006) 112: 958-967). For breeding methods in general see Principles of Plant Genetics and Breeding, 2007, George Acquaah, Blackwell Publishing, ISBN-13: 978-1-4051-3646-4.

The invention thus also provides a method of introducing a single locus conversion, or single trait conversion or introducing a desired trait, into a onion plant according to the invention and/or into NUN 08003 ON comprising:

(a) crossing a onion plant of variety NUN 08003 ON, a representative sample of seed of said variety having been deposited under Accession Number NCIMB 42621, with a second onion plant comprising a desired single locus to produce F1 progeny plants;

(b) selecting F1 progeny plants that have the single locus;

(c) crossing the selected progeny plants with a plant of NUN 08003 ON, to produce backcross progeny plants;

(d) selecting backcross progeny plants that have the single locus and one or more (or all) distinguishing characteristics of onion according to the invention and/or all the physiological and morphological characteristics of NUN 08003 ON to produce selected backcross progeny plants; and (e) optionally repeating steps (c) and (d) one or more times in succession to produce selected second, third or fourth or higher backcross progeny plants that comprise the single locus and otherwise one or more (or all) the distinguishing characteristics of the onions according to the invention and/or comprise all of the physiological and morphological characteristics of NUN 08003 ON, when grown in the same environmental conditions. The invention further relates to plants obtained by this method.

The above method is provided, wherein the single locus confers a trait, wherein the trait is pest resistance or disease resistance.

In one embodiment the trait is disease resistance and the resistance is conferred to Black Mold, Neck Mold, Puple Blotch, Smut, Mildew, Pink root, Smudge, Yellow dwarf and *Thrips*.

The invention also provides a onion plant comprising at least a first set of the chromosomes of onion variety NUN 08003 ON, a sample of seed of said variety having been deposited under Accession Number NCIMB 42621; optionally further comprising a single locus conversion, wherein said plant has essentially all of the morphological and physiological characteristics of the plant comprising at least a first set of the chromosomes of onion NUN 08003 ON. In another embodiment, this single locus conversion confers a trait selected from the group consisting of male sterility, herbicide tolerance, pathogen resistance (e.g., insect resistance, nematode resistance, resistance to bacterial, fungal, and viral disease), environmental stress tolerance, modified carbohydrate metabolism, modified protein metabolism improved harvest characteristics, enhanced nutritional quality, increased antioxidant content, improved processing characteristics, high yield, improved characteristics related to the bulb flavor, texture, size, shape, durability, shelf life, and yield, increased soluble solids content, uniform ripening, delayed or early ripening, adaptability for soil conditions, and adaptability for climate conditions In one embodiment, NUN 08003 ON may also be mutated (by e.g. irradiation, chemical mutagenesis, heat treatment, etc.) and mutated seeds or plants may be selected in order to change one or more characteristics of NUN 08003 ON. Methods such as TILLING may be applied to onion populations in order to identify mutants. Similarly, NUN 08003 ON may be transformed and regenerated, whereby one or more chimeric genes are introduced into the variety or into a plant comprising all but 1, 2, 3, or more of the morphological and physiological characteristics (e.g. as listed in Table 1 and/or 2). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 08003 ON, or progeny thereof, by transforming NUN 08003 ON or progeny thereof with a transgene that confers the desired trait, wherein the transformed plant retains all the phenotypic and/or morphological and/or physiological characteristics of NUN 08003 ON or the progeny thereof and contains the desired trait.

The invention also provides for progeny of onion hybrid (F1) variety NUN 08003 ON obtained by further breeding with NUN 08003 ON. In one aspect progeny are F2 progeny obtained by crossing NUN 08003 ON with another plant or S2 progeny obtained by selfing NUN 08003 ON. Also encompassed are F3 progeny obtained by selfing the F2 plants. "Further breeding" encompasses traditional breeding (e.g., selfing, crossing, backcrossing), marker assisted breeding, and/or mutation breeding. In one embodiment, the progeny have one or more (or all) of the distinguishing characteristics mentioned further above when grown under the same environmental conditions. In a further embodiment the progeny have all the physiological and morphological characteristics of variety NUN 08003 ON when grown under the same environmental conditions. In another embodiment the progeny have one, two, or three distinct traits (qualitative or quantitative) introduced into NUN 08003 ON, while retaining all the other physiological and morphological characteristics of variety NUN 08003 ON when grown under the same environmental conditions.

The invention also provides a plant having one, two or three physiological and/or morphological characteristics which are different from those of NUN 08003 ON and which otherwise has all the physiological and morphological characteristics of NUN 08003 ON, wherein a representative sample of seed of variety NUN 08003 ON has been deposited under Accession Number NCIMB 42621. In particular plants which differ from NUN 08003 ON in none, one, two or three of the characteristics mentioned in Table 1 and/or 2 are encompassed.

In one aspect, the plant having one, two or three physiological and/or morphological characteristics which are different from those of NUN 08003 ON and which otherwise has all the physiological and morphological characteristics of NUN 08003 ON differs from NUN 08003 ON in one, two or three of the distinguishing morphological and/or physiological characteristics selected from 1) bulb height; 2) bulb diameter; 3) Sheath column length (height from soil line to base of lowest succulent leaf); 4) Plant height above soil line to highest point of any foliage; 5) adaptation range; 6) sheath diameter (at mid-length); 7) bulb weight; 8) maturity; and 9) leaf thickness.

In another embodiment the plant having one, two or three physiological and/or morphological characteristics which are different from those of NUN 08003 ON and which otherwise has all the physiological and morphological characteristics of NUN 08003 ON differs from NUN 08003 ON in one, two or three morphological or physiological characteristic other than the "distinguishing morphological and/or physiological characteristics" (or essential physiological and/or morphological characteristics) of NUN 08003 ON selected from: 1) bulb height; 2) bulb diameter; 3) Sheath column length (height from soil line to base of lowest succulent leaf); 4) Plant height above soil line to highest point of any foliage; 5) adaptation range; 6) sheath diameter (at mid-length); 7) bulb weight; 8) maturity; and 9) leaf thickness.

Onions according to the invention, such as the variety NUN 08003 ON, or its progeny, or a plant having all physiological and/or morphological characteristics but one, two or three which are different from those of NUN 08003 ON, can also be reproduced using vegetative reproduction methods. Therefore, the invention provides for a method of producing plants, or a part thereof, of variety NUN 08003 ON, comprising vegetative propagation of variety NUN 08003 ON. Vegetative propagation comprises regenerating a whole plant from a plant part of variety NUN 08003 ON (or from its progeny or from or a plant having all physiological and/or morphological characteristics but one, two or three, which are different from those of NUN 08003 ON), such as a cutting, a cell culture or a tissue culture.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets The invention also provides for a vegetatively propagated plant of variety NUN 08003 ON (or from its progeny or from or a plant having all but one, two or three physiological and/or morphological characteristics which are different from those of NUN 08003 ON, or a part thereof, having one or more distinguishing characteristics and/or all the morphological and physiological characteristics of NUN 08003 ON (except for the characteristics differing), when grown under the same environmental conditions.

Parts of NUN 08003 ON (or of its progeny or of a plant having all physiological and/or morphological characteristics but one, two or three which are different from those of NUN 08003 ON) encompass any cells, tissues, organs obtainable from the seedlings or plants, such as but not limited to: onion bulbs or parts thereof, cuttings, hypocotyl, cotyledon, pollen, scales and the like. Such parts can be stored and/or processed further. Encompassed are therefore also food or feed products comprising one or more of such identifiable parts, such as canned, chopped, cooked, roasted, preserved, frozen, fried, dried, pickled, or pureed onion bulbs from NUN 08003 ON or from progeny thereof, such as a plant having all but one, two or three physiological and/or morphological characteristics which are different from those of NUN 08003 ON.

In one aspect haploid plants and/or double haploid plants of NUN 08003 ON, or a plant having all but one, two or three physiological and/or morphological characteristics which are different from those of NUN 08003 ON, or progeny of any of these, are encompassed herein. Haploid and double haploid (DH) plants can, for example, be produced by cell or tissue culture and chromosome doubling agents and regeneration into a whole plant. For DH production chromosome doubling may be induced using known methods, such as colchicine treatment or the like.

Also provided are plant parts derived from variety NUN 08003 ON (or from its progeny or from a plant having all but one, two or three physiological and/or morphological characteristics which are different from those of NUN 08003 ON D), or from a vegetatively propagated plant of NUN 08003 ON (or from its progeny or from a plant having all but one, two or three physiological and/or morphological characteristics which are different from those of NUN 08003 ON), being selected from the group consisting of: harvested bulbs or parts thereof, pollen, cells, leaves or parts thereof, petioles, cotyledons, hypocotyls, shoots or parts thereof, stems or parts thereof, or vines or parts thereof, roots or parts thereof, cuttings, or flowers.

In one embodiment, the invention provides for extracts of a plant described herein and compositions comprising or consisting of such extracts. In a preferred embodiment, the extract consists of or comprises tissue of a plant described herein or is obtained from such tissue.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

The invention also provides for a food or feed product comprising or consisting of a plant part described herein wherein the plant part can be identified as a part of the plant of the invention. Preferably, the plant part is a onion bulb or part thereof and/or an extract from a bulb or another plant part described herein. The food or feed product may be fresh or processed, e.g., dried, grinded, powdered, pickled, chopped, cooked, juiced, preserved, pickled, fried, canned, steamed, boiled, blanched and/or frozen, etc.

In a preferred embodiment, the present invention and/or embodiments thereof relate to food and o/or a food product (or a feed) comprising a part of the onion plant of the invention NUN 08003 ON (e.g. a bulb or a seed) wherein the genotype of the plant of the invention is present so that the plant or plant part of the invention can still be identified. Methods to identify the genotype of an onion plant are known in the art and include nucleotide sequence alignment or using molecular markers.

Containers such as cans, boxes, crates, bags, cartons, Modified Atmosphere Packagings, films (e.g. biodegradable films), etc. comprising plant parts of plants of NUN 08003 ON (fresh and/or processed) described herein are also provided herein.

Marketable onion bulbs are generally sorted by size and quality after harvest. Alternatively the onion bulbs can be sorted by pungency or sugar content.

Using methods known in the art like "reverse breeding", it is possible to produce parental lines for a hybrid plant such as NUN 08003 ON; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi:10.1038/nprot.2014.049, which are enclosed by reference. Such method for producing parental lines for a hybrid organism, comprises the steps of:

a) defining a set of genetic markers that are present in a heterozygous form (H) in a partially heterozygous starting organism;
b) producing doubled haploid lines from spores of the starting organism:
c) genetically characterizing the doubled haploid lines thus obtained for the said set of genetic markers to determine whether they are present in a first homozygous form (A) or in a second homozygous form (B);
d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 08003 ON) comprising the step of making double haploid cells from haploid cells from the plant of the invention (NUN 08003 ON) or a seed of that plant; and optionally crossing these parental lines to produce and collect seeds. In another aspect, the invention relates to a combination of parental lines produced by this method. In still another aspect said combination of parental lines can be used to produce a seed or plant of NUN 08003 ON when these parental lines are crossed. In still another aspect, the invention relates to a combination of parental lines from which a seed or plant having all but one, two or three physiological and/or morphological characteristics of NUN 08003 ON can be produced; or in another aspect, wherein a seed or plant having the distinguishing characteristics 1)-5) or 1)-9) of NUN 08003 ON, as herein defined, can be produced when grown under the same environmental conditions. In still another aspect, the invention relates to a combination of parental lines from which a seed or plant having all the characteristics of NUN 08003 ON as defined in Table 1 and/or 2 can be produced when grown under the same conditions.

REFERENCES

The following references, to the extent that they provide exemplary procedural or other details supplementary to those set forth herein, are specifically incorporated herein by reference:

Choi et al., Plant Cell Rep., 13: 344-348, 1994.

Dunstan and Short (1977) Physiol, Plant, 41: 70-72

SANTOS, CAF et al. Genetic similarity among onion cultivars of different types and origins, based on AFLP markers. Hortic. Bras. [online] 2011, vol. 29, n. 1, pp. 32-37. ISSN 0102-0536. dx.doi.org/10.1590/S0102-05362011000100006.

Pike and Yoo, Scientia Horticulturae, 45 (1990) 31-36

Ellul et al., Theor. Appl. Genet., 107:462-469, 2003.

Deposit Information

A total of 2500 seeds of the hybrid variety NUN 08003 ON were deposited according to the Budapest Treaty by Nunhems B. V. on Aug. 9, 2016, at the American Type Culture Collection (ATCC), 10801 University Boulevard, Manassas, Va. 20110-2209 USA or at the NCIMB Ltd., Ferguson Building, Craibstone Estate, Bucksburn, Aberdeen AB21 9YA, United Kingdom (NCIMB). The deposit has been assigned Accession Number NCIMB 42621.

A deposit of NUN 08003 ON and of the male and female parent line is also maintained at Nunhems B. V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

All references cited herein are hereby expressly incorporated herein by reference.

Characteristics of NUN 08003 ON

Cometa is considered to be the most similar variety to NUN 08003 ON. Cometa is a commercial variety from Nunhems. In Table 1 and 2 a comparison between NUN 08003 ON and Cometa is shown based on a trial in the USA. Trial location: Parma, Id., USA (43748539-116986286). Planting date: Mar. 18, 2015, harvest date Aug. 20, 2015.

Two replications of 15 plants each, from which 20 plants or plant parts were randomly selected, were used to measure characteristics. In Table 1 the USDA descriptors of NUN 08003 ON (this application) and reference Cometa (commercial variety) are listed. In Table 2, additional descriptors of NUN 08003 ON and reference Cometa are summarized.

TABLE 1

| Comparison of USDA descriptors between NUN 08003 ON and Cometa | | |
|---|---|---|
| Descriptor | Application Variety NUN 08003 ON | Comparison Variety COMETA |
| 1. TYPE: | | |
| 1 = Bulb 2 = Bunching | 1 | 1 |
| 1 = short day; 2 = long day | 2 | 2 |
| Adaptation range (degree mean latitude) | 35-48 | 30-48 |
| Maturity (days): 1 = early (75-90); 2 = medium (100-120); 3 = late (>130) | 2 (120) | 2 (125) |
| 2. PLANT: | | |
| Height above soil line to highest point of any foliage | 88.6 cm | 94.3 cm |
| Shorter than comparison variety | 5.7 cm | — |
| Plant 1 = erect (Spartam Gem); 2 = intermediate; 3 = floppy (Epoch) | 1 | 1 |
| 3. LEAF: | | |
| Length (before maturity yellowing begins) cm | 66 | 69 |
| Width mm | 26 | 26 |
| Thickness (at mid-length of longest leaf) mm | 2.4 | 2.8 |
| Color: 1 = light green (Early Grano); 2 = medium green (Yellow Bermuda); 3 = blue green (Australian Brown U.C. No. 1) | 2 | 1 |
| Color Chart Code (RHS Color Chart) | Green N 137 A | Green N 137 D |
| Bloom: 1 = none-glossy; 2 = light (Early Grano); 3 = medium (Crystal Wax); 4 = heavy (California Early Red) | 2 | 2 |
| 4. SHEATH: | | |
| Column length mm (height from soil line to base of lowest succulent leaf) | 17.9 | 19.5 |
| Diameter mm (at mid-length) | 19.5 | 27 |
| Scape: cm (From soil line to base of inflorescence) | NA | NA |
| Scape: mm (diameter at mid-length) | NA | NA |
| 5. INFLORESCENCE: | | |
| Pollen Viability (1 = sterile; 2 = fertile) | 1 | 1 |
| 6. BULB: | | |
| Average number bulbs per meter | n.r. | n.r. |
| Size (harvested): 1 = small (Red Creol); 2 = medium (Australian Brown U.C. No. 1); 3 = large (Early Grano) | 3 | 3 |
| Shape: 1 = Globe (White Sweet Spanish); 2 = Deep Globe (Abundance); 3 = Flt. Globe (Australian Brn. U.C. No. 1); 4 = Top Shape (Texas Grano 502); 5 = Deep Flat (Granex); 6 = Thick Flat (Ebenezer); 7 = Flat (Crystal Wax); 8 = Torpedo-Long Oval (Italian Red) | 1 | 1 |
| Height: cm | 8.6 | 7.9 |
| Diameter: cm | 8.7 | 8.0 |
| Shape Index | .99 | .99 |
| 1 = invaginate; 2 = evaginate | NA | n.r. |
| Color (skin): 01 = Brown (Australian Brn. U.C. No. 1); 02 = Purplish Red (Italian Red); 03 = Buff Red (Red Creole); 04 = Pinkish Yellow (Ebenezer); 05 = Brownish Yellow (Mt. Danvers); 06 = Deep Yellow (Brigham Yellow Globe); 07 = Medium Yellow (Early Yellow Globe); 08 = Pale Yellow (Yellow Bermuda); 09 = White (White Sweet Spanish); 10 = Other (Specify) _____ | 09 (RHS white NN155B) | 09 (RHS white NN155B) |
| Color (interior): 1 = Pink; 2 = Red; 3 = Purplish Red; 4 = White; 5 = Cream; 6 = Light Green-Yellow; 7 = Dark Green-Yellow | 4 (RHS yellow-white 158D) | 4 (RHS yellow-white 158D) |
| Scales: 1 = Few (Crystal Wax); 2 = Medium (Australian Brown U.C. No. 1); 3 = Many (Sweet Spanish) | 2 | 2 |
| Scales: 1 = Thick (Australian Brown U.C. No. 1); 2 = Medium (Red Creole); 3 = Thin (Crystal Wax) | 2 | 2 |
| Scale retention: 1 = Very Good (Australian Brn. U.S. No. 1); 2 = Good (Ebenezer); 3 = Fair (Red Wethersfield); 4 = Poor (Crystal Wax) | 2 | 2 |
| Pugence: 1 = Mild (Early Grano); 2 = Medium (Crystal Wax); 3 = Strong (White Creole) | 3 | 3 |
| Storage: 1 = Good (Ebenezer); 2 = Fair (Yellow Globe Danvers); 3 = Poor (Crystal Wax) | 1 | 1 |

TABLE 1-continued

Comparison of USDA descriptors between NUN 08003 ON and Cometa

| Descriptor | Application Variety NUN 08003 ON | Comparison Variety COMETA |
|---|---|---|
| 7. DISEASE RESISTANCE 0 = not tested; 1 = susceptible 2 = resistant | | |
| 8. INSECT RESISTANT 0 = not tested; 1 = susceptible 2 = resistant | | |

TABLE 2

Comparison of non-USDA descriptors between NUN 08003 ON and Cometa

| Descriptor | Applcation Variety NUN 08003 ON | Comparison Variety COMETA |
|---|---|---|
| Bulb weight (gram) | 329.5 | 253.3 |

Table 1 and 2 contain typical values. Values may vary due to environment. Other values that are substantially equivalent are also within the scope of the invention. N.A.=not applicable; n.r.=not recorded.

The invention claimed is:

1. A plant or seed of onion variety NUN 08003 ON, wherein a representative sample of said seed has been deposited under Accession Number NCIMB 42621.

2. A plant part of the plant of claim 1, defined as a leaf, pollen, a bulb, a scale, an ovule, a fruit, a cutting, umbel, flower or a part of any of these, or a cell.

3. A seed grown on the plant of claim 1.

4. An onion plant, or a part thereof which comprises the characteristics of the plant of claim 1 described in Table 1.

5. A tissue or cell culture of regenerable cells of the plant of claim 1.

6. The tissue or cell culture according to claim 5, comprising cells or protoplasts from a plant part selected from the group consisting of embryos, meristems, cotyledons, hypocotyl, pollen, leaves, bulbs, scales, anthers, roots, root tips, pistil, petiole, flower, fruit, seed, stem and stalks.

7. An onion plant regenerated from the tissue or cell culture of claim 5, wherein the plant has all of the physiological and morphological characteristics of the plant of NUN 08003 ON, wherein a representative sample of said seed has been deposited under Accession Number NCIMB 42621.

8. A method of producing of the plant of claim 1, or a part thereof, comprising vegetative propagation of the plant of claim 1.

9. The method of claim 8, wherein said vegetative propagation comprises regenerating a whole plant from a part of the plant of claim 1.

10. The method of claim 9, wherein said part is a bulb or bulblet, a cutting, a cell culture or a tissue culture.

11. A vegetative propagated plant of claim 1, or a part thereof, wherein the plant has all of the physiological and morphological characteristics of the plant of claim 1 when determined at the 5% significance level.

12. A method of producing an onion plant, said method comprising crossing the plant of claim 1 with a second onion plant one or more times, and selecting progeny from said crossing and optionally allowing the progeny to form seed.

13. A mutant onion plant having one, two or three physiological and/or morphological characteristics which are different from those of the plant of claim 1 and which otherwise has all the physiological and morphological characteristics of the plant of claim 1 as listed in Table 1.

14. A food or feed product, comprising the plant part of claim 2 wherein the plant part can be identified as a part of the plant of claim 1.

15. The plant of claim 1 further comprising a single locus conversion, wherein said plant has all or all but one, two or three of the morphological and physiological characteristics of the plant of claim 1, optionally wherein the single locus conversion confers a trait selected from the group consisting of male sterility, herbicide tolerance, insect resistance, pest resistance, disease resistance, environmental stress tolerance, modified carbohydrate metabolism and modified protein metabolism.

16. A container comprising the bulb, bulblet or seed of the plant of claim 1.

17. A method of producing a combination of parental lines of the plant of claim 1 comprising the step of producing at least one further generation from the plant of claim 1 or a seed of claim 1.

\* \* \* \* \*